United States Patent [19]

Kagayama

[11] 4,349,631
[45] Sep. 14, 1982

[54] PROCESS FOR PRODUCING HEAT-RESISTANT ACETATE KINASE
[75] Inventor: Masao Kagayama, Uji, Japan
[73] Assignee: Unitika Ltd., Hyogo, Japan
[21] Appl. No.: 209,096
[22] Filed: Nov. 21, 1980
[30] Foreign Application Priority Data
Nov. 22, 1979 [JP] Japan ................ 54-151660
[51] Int. Cl.³ .................... C12N 9/12; C12R 1/07
[52] U.S. Cl. ............................ 435/194; 435/832
[58] Field of Search ............ 435/243, 194, 832
[56] References Cited
FOREIGN PATENT DOCUMENTS
52-25088 2/1977 Japan ..................... 435/194

OTHER PUBLICATIONS
Nakajima et al. Purification And Properties Of Acetate Kinase From *Bacillus stearothermophilus* 1978 Journal Of Biochemistry 84 pp. 193–203.
Rose, Acetate Kinase Of Bacteria, Methods in Enzymology vol. I 1955 pp. 591–595.

*Primary Examiner*—Raymond N. Jones
*Assistant Examiner*—John E. Tarcza
*Attorney, Agent, or Firm*—Sughrue, Mion, Zinn, Macpeak & Seas

[57] ABSTRACT

A process for producing a heat-resistant acetate kinase is described, comprising culturing cells of Strain UK 788 (FERM-P No. 5141), a new strain of thermophilic *Bacillus stearothermophilus* having an appreciably elongated cell and recovering a heat-resistant acetate kinase from the culture obtained. According to the process, a heat-resistant acetate kinase can be produced efficiently on an industrial scale.

11 Claims, 2 Drawing Figures

FIG. I

PROCESS FOR PRODUCING HEAT-RESISTANT ACETATE KINASE

BACKGROUND OF THE INVENTION

This invention relates to a process for producing a heat-resistant acetate kinase.

Acetate kinase is an enzyme widely used for the synthesis of adenosine triphosphate, a source of biological energy, from acetylphosphoric acid and adenosine diphosphate, or for determination of the acetic acid levels in foods. Acetate kinase is usually obtained as a purified enzyme from *Escherichia coli* (see Journal of *Biological Chemistry*, 211, p. 737, 1954, and *Methods in Enzymology*, 1, p. 591), but the acetate kinase isolated from *Escherichia coli* is very unstable and not suitable for use on an industrial scale.

Japanese Patent Application (OPI) No. 25088/77 (the term "OPI" as used herein means a published unexamined Japanese patent application) describes a process for producing a highly heat-resistant (i.e., heat-stable) acetate kinase from a thermophilic bacterium *Bacillus stearothermophilus*. But since the acetate kinase produced is an endoenzyme, cultured cells must be first collected by centrifugation or other suitable means before the desired enzyme can be extracted from the cells by ultrasonic treatment or physical breaking.

Since bacterial cells are smaller in size than yeast or fungal cells, they are difficult to collect from the culture, so they are usually collected by centrifugation rather than by filtration. But the rate of sedimentation of cells in centrifugation is proportional to the square of the cell diameter (see Sekiyu Hakko, *Petroleum Fermentation*, p. 102, 1970, Saiwai Publishing Company), so the recovery of bacterial cells from the fermentation broth is more difficult and expensive than recovery of yeast and fungal cells, and is very disadvantageous in an industrial operation. According to the estimate by Daniel I. C. Wang, the cost of recovery of bacteria is about 3.8 times the cost of recovery of yeast (see *Chemical Engineering*, Vol. 15, p. 99, 1968).

Therefore, several methods have been proposed for improving the recovery of bacterial cells. Among the proposed methods is a method including flocculation of cells with a flocculant such as ferric chloride, calcium chloride or polymeric flocculant, and a method of modifying the cell protein to an easily collectable form by heating or treatment with a strong acid or base. These techniques are effective when the cell is not the end product, but when the cell per se or the components in the cell are the end product, they are not effective because the flocculant contaminates the product, or the components in the cell are denatured. Furthermore, bacteria belonging to the genus Bacillus have a relatively hard cell wall which can be broken only slightly. Therefore, the efficiency in extraction of intracellular components is low. For these reasons, the techniques proposed to date for recovery of bacterial cells are not suitable for use in industrial large-scale production.

SUMMARY OF THE INVENTION

The primary object of this invention is to provide a process for producing a heat-resistant acetate kinase that enables the industrial large-quantity production of a heat-resistant acetate kinase.

To achieve this object, we conducted a screening of naturally occurring microorganisms by Koch's plate culture (for example, see William Burroros, *Textbook of Microbiology*, 19th Ed., p. 21, ed. by W. B. Saunders Company, U.S.A.) in search for a thermophilic bacterium having an easily settleable cell and an easily breakable cell wall. As a result, we found a new strain in manure in Ogura, Uji, Kyoto, Japan. In consideration of its properties, the strain is believed to belong to *Bacillus stearothermophilus*, but the cell is extremely elongated and is several to several tens of times larger than the cell of known *Bacillus stearothermophilus* described in *Bergey's Manual of Determinative Bacteriology*. We have found that the new strain is a thermophilic microorganism that produces acetate kinase and which has an easily settleable cell and an easily breakable cell wall.

Therefore, this invention provides a process for producing a heat-resistant acetate kinase that comprises culturing a biologically pure culture of Strain UK 788 (FERM-P No. 5141), which identifies the new strain of thermophilic *Bacillus stearothermophilus* noted above having an appreciably elongated cell, and recovering a heat-resistant acetate kinase from the culture obtained. According to this invention, a heat-resistant acetate kinase can be produced efficiently on an industrial scale.

DETAILED DESCRIPTION OF THE INVENTION

Figure 1:
FIG. 1 is a micrograph (150×) of the cells of the strain of this invention and type culture *Bacillus stearothermophilus* IAM 11001 after culturing on a nutrient agar slant culture at 60° C. for 24 hours.

The mycological properties of a biologically pure culture of Strain UK 788 (FERM-P No. 5141) of *Bacillus stearothermophilus* are described below. For the methods and the compositions of media used in the determination of mycological properties, see the *Manual of Microbiological Methods*, 1957, ed. by Society of American Bacteriologists, McGraw-Hill Book Company, *Biseibutsu no Bunrui to Dotei* (Classification and Identification of Microorganisms), 1975, ed. by Takeharu Hasegawa, Tokyo Daigaku Shuppan-Kai, and *Baichigaku Kakuron* (Study of Culture Media), 1967, by Toshiichi Sakazaki, Naya Publishing Company. When an agar medium was used in such determinations, it contained 3 wt% of agar.

Morphological observation: Culture at 60° C. for 24 hours
1. Shape and size of cell: Very long rods, filamentous, 0.8–1.2×10 to more than a hundred microns, sometimes more than several hundred microns
2. Pleomorphism: None
3. Motility: None
4. Spores: Cylindrical endospores formed in the center or on the tip of the cell. No bulging sporangia.
5. Gram stain: Positive
6. Acid-fast straining: None State of growth: Culture at 60° C. for 24 hours
1.
   Broth-agar plate culture
   Shape: Circular
   Periphery: Undulate
   Elevation: Flat
   Gloss: None
   Surface: Rough Appearance: Semitransparent
2. Broth-agar slant culture
Growth: Good
Shape: Filamentous
3. Broth liquid culture
Surface growth: Slight ring formation
Turbidity: Strong
Precipitate: Small
Coloring and decoloring: None
4. Broth-gelatin stab culture
A broth containing 30% gelatin was subjected to stab culture at 60° C. for a suitable period, followed by cooling to see if the culture was solidified: Gelatin was liquefied.
5. Broth-gelatin stab culture
Shape: Beaded
Surface growth: Good
6. Litmus milk: Litmus discoloration occurred at pH 6.0.
Milk first solidified, then liquefied.

Physiological properties: Culture at 60° C. for 1 to 2 days
1. Reduction of nitrate: Yes
2. Denitrifying reaction: Negative
3. MR test: Positive
4. VP test: Positive
5. Indole formation: None
6. Hydrogen sulfite formation: None
7. Starch hydrolysis: Yes
8. Utilization of citric acid: None
9. Utilization of nitrate: Yes
10. Utilization of ammonium salt: Yes
11. Pigment formation: None
12. Urease activity: None
13. Oxidase activity: Yes
14. Catalase activity: Yes
15. Growth pH: 5.0–8.5
   Optimum pH: 6.0–7.5
16. Growth temperature: 40°–70° C.
   Optimum temperature: 50°–63° C.
17. Behavior with respect to oxygen: Grows well aerobically and grows slightly even under anaerobic conditions.
18. O-F test: Negative
19. Determination of phenylalanine: Negative
20. Sodium chloride fastness: Grows with 5% NaCl but cannot grow with 7% NaCl.
21. Vitamin requirement: None
22. Tyrosine decomposition: None.

Formation of acid and gas from carbon source: Culture at 60° C. for 1 to 2 days;

|   |             | Acid | Gas |
|---|-------------|------|-----|
| 1.  | L-arabinose | –    | –   |
| 2.  | D-xylose    | +    | –   |
| 3.  | D-glucose   | +    | –   |
| 4.  | D-mannose   | +    | –   |
| 5.  | D-fructose  | +    | –   |
| 6.  | D-galactose | –    | –   |
| 7.  | Maltose     | +    | –   |
| 8.  | Sucrose     | –    | –   |
| 9.  | Lactose     | –    | –   |
| 10. | Trehalose   | +    | –   |
| 11. | D-sorbitol  | –    | –   |
| 12. | D-mannitol  | –    | –   |
| 13. | Innositol   | –    | –   |
| 14. | Glycerin    | –    | –   |
| 15. | Starch      | –    | –   |

These mycological properties generally agree with those of *Bacillus stearothermophilus* described in Bergey's *Manual of Determinative Bacteriology*, 8th Ed. We therefore compared the strain of this invention with the following type cultures of *Bacillus stearothermophilus*, IAM 11001, 11002, 11003, 11004 (stored at Institute of Applied Microbiology, the University of Tokyo) and IFO12550 (stored at Institute for Fermentation, Osaka). The new strain UK 788 defined from the type cultures with respect to two or three physiological properties. The biggest difference is in the size of the cell, as is clearly seen from Table 1 and FIG. 1. FIG. 1 is a micrograph (150×) of the cells of new strain UK 788 and type culture IAM 11001 that were subjected to nutrient agar slant culture at 60° C. for 24 hours. In the micrograph, the cell of new strain UK 788 is seen as a much elongated filament, and the cell of the type culture is seen as a dot or short rod.

The strain of this invention has a cell much more elongated than the cell of the type culture of *Bacillus stearothermophilus*, and *Bacillus stearothermophilus* having a cell comparable to the cell of UK 788 is not described in Bergey's Manual, loc. cit., or any other reports. We therefore concluded that the strain used in this invention is completely new, and named it, as indicated above, *Bacillus stearothermophilus* UK 788 (hereinafter referred to as "FERM-P No. 5141"). The strain was a biologically pure culture and was deposited with the Fermentation Research Institute Agency of Industrial Science and Technology, the Ministry of International Trade and Industry (at No. 1-3, Higashi 1-Chome, Yatabe-Machi, Tsukuba-Gun, Ibaragi, Japan) on Aug. 10, 1979 under a receipt number FERM-P No. 5141.

TABLE 1

Cell Size of UK 788 (FERM-P No. 5141) and Type Cultures of *Bacillus stearothermophilus*

| Strain | Cell Size* |
|--------|-----------|
| UK 788 | 0.8–1.2 × 10 to more than a hunderd microns, and sometimes more than several hundreds of microns |
| IAM 11001 | 0.8–1.0 × 2 to 8 microns |
| IAM 11002 | 0.6–0.8 × 2 to 5 microns |
| IAM 11003 | 0.6–1.0 × 2 to 8 microns |
| IAM 11004 | 0.6–1.0 × 1.5 to 5 microns |
| IFO 12550 | 0.6–1.0 × 2 to 8 microns |

*The figures were those obtained after nutrient agar slant culture at 60° C. for 24 hours.

Common media for cultivation of bacteria may be used in culturing strain FERM-P No. 5141, and a liquid medium is preferred. The medium can contain a variety of nutrient sources; carbon sources include sugars such as glucose, sucrose, fructose, starch hydrolyzate, molasses and sulfite pulp liquor, organic acids such as acetic acid and lactic acid, and also alcohols, fats and oils, aliphatic acids, and glycerin that can be assimilated by FERM-P No. 5141, nitrogen sources include inorganic or organic materials such as ammonium sulfate, ammonium chloride, ammonium phosphate, uric acid, ammonia, nitrate, amino acid, peptone, meat extract and yeast extract, inorganic salts such as potassium, sodium, phosphoric acid, zinc, iron, magnesium, manganese, copper, calcium, and cobalt salts. Optionally, traces of metals, corn steep liquor, vitamins, nucleic acid, etc., may also be used. Nutrient sources commonly utilized by bacteria may be used. On a medium containing these nutrient sources, the strain FERM-P No. 5141 of this invention is cultured aerobically for from about 2 to 6 hours, generally at from about 20° to 80° C., preferably at from 40° to 70° C., and more preferably at from 50° to 63° C. Cells containing a heat-resistant acetate kinase can be obtained by either batch culture or continuous culture. Batch culture is preferably continued to the last stage of the logarithmic growth phase. Continuous culture is preferably conducted by the substance environmental-type continuous cultivation method (chemostat; Herbert D., Elsworth R. and Telling R. C., *Journal of General Microbiology*, Vol. 14, No. 8, pp. 601–622, 1956) and cells having a high content of heat-resistant acetate kinase can be obtained by adjusting the dilution ratio (the rate of supply of liquid medium to fermentation tank and withdrawal therefrom divided by the volume of liquid medium in the fermentation tank) close to the maximum specific growth rate of FERM-P No. 5141.

A heat-resistant acetate kinase can be isolated and purified from the culture by the following procedures: the cells are first collected from the culture by centrifugation or filtration, i.e., the treatment of collecting the cells is industrially carried out by centrifuging the culture with Sharples or De Laval type centrifuge, or by filtering the culture by means of a constant-pressure filtration or a rotating drum filtration (see *Biochemical Engineering*, Second Edition, pp. 349–355, 1973, ed. by Shuichi Aiba, Arthur E. Humphrey, Nancy F. Millis, University of Tokyo Press), and the collected cells are subjected to a conventional enzyme isolation and purification technique, i.e., the cells are crushed and centrifuged to provide a supernatant which is either fractionated with an organic solvent or a variety of salts such as sodium chloride, magnesium sulfate, ammonium sulfate, sodium sulfate, potassium phosphate, sodium citrate, and so forth, or purified by adsorption on a carrier.

One example of such a conventional technique is described in *Journal of Biochemistry*, Vol. 84, No. 1, pp. 193–203, 1978. A heat-resistant acetate kinase obtained can be purified by the technique described in *Journal of Biochemistry*, loc. cit., and the physicochemical properties of the resulting crystal and the mechanism of its action can be compared with the crystal obtained from those of other strains of *Bacillus stearothermophilus*. Doing so, it has been found that the acetate kinase obtained according to the present invention has the same properties as the heat-resistant acetate kinase described in *Journal of Biochemistry*, loc. cit., and Japanese Patent Application (OPI) No. 25088/77.

The cells of FERM-P No. 5141 cultured and harvested by the method of this invention are very easy to collect, and the centrifugation time that was 10 minutes at 8,000 G with previously known strains of *Bacillus stearothermophilus* is reduced to about a fifth. Another great advantage of using cells of FERM-P No. 5141 is that it permits previously impractical cell collection by filtration through a filter medium to be used.

Furthermore, whereas the cells of the known strains of *Bacillus stearothermophilus* required 15 minutes of ultrasonic treatment (Frequency: 10 KHz, Output: 200 W) to break, the collected cells of FERM-P No. 5141 can be equally broken by an ultrasonic treatment that lasts for only about 3 minutes under the same conditions. This also presents a significant advantage in the industrial production of heat-resistant acetate kinase.

The content of the heat-resistant acetate kinase produced by the process of this invention is measured by the reverse reaction system described in *Journal of Biological Chemistry*, 249, p. 2567, 1974: changes in ATP are converted to changes in nicotinamide adenine dinucleotide reduced form (hereunder referred to as NADH) and these changes are traced by absorbance at 340 nm. The enzymatic activity required to reduce the absorbance of 1 micromol of NADH at 340 nm per minute is defined to be one unit (hereunder referred to as U).

This invention is now described in greater detail by reference to the following examples which are given here for illustrative purposes only and are not intended to limit the scope of the invention.

EXAMPLE 1 AND COMPARATIVE EXAMPLE 1

A 500-ml conical flask was charged with 100 ml of a medium prepared by dissolving in one liter of tap water a mixture of 2 g of glucose, 2 g of $(NH_4)_2SO_4$, 1 g of yeast extract (Difco), 1 g of $KH_2PO_4$, 1 g of $Na_2HPO_4.12H_2O$ and 0.1 g of $MgSO_4.7H_2O$, closed up with a cotton stopper, and sterilized with pressurized steam (121° C., 1 atm.) for 10 minutes. The medium was cooled to 50° C. and inoculated with *Bacillus stearothermophilus* UK 788 (FERM-P No. 5141) grown on an agar slant medium of the same formulation as indicated above, and subjected to rotary shake cultivation in a rotary shaker (RGR No. 2 shaker of Takasaki Seisakusho, 180 rpm) at 55° C. After conducting the rotary shake cultivation for 5 hours, when the growth of cells was observed, the turbidity of the medium had an absorbance of 0.1 at 660 nm (measured by 101-type spectrophotometer produced by Hitachi Ltd.) and the growth of cells entered the last stage of the logarithmic growth phase, the cultivation was stopped and the cells were collected by centrifugation for 2 minutes at 8,000 G. The yield was 6 g of wet cells per liter. One gram of the wet cells was suspended in 20 ml of 0.1 M phosphate buffer (pH 7.0) and the protein that leaked from the cells treated with an ultrasonic breaker (Model 200 M of Kubota Medical Appliance Supply Corp., Frequency: 10 KHz, Output: 200 W) was measured.

Figure 2:
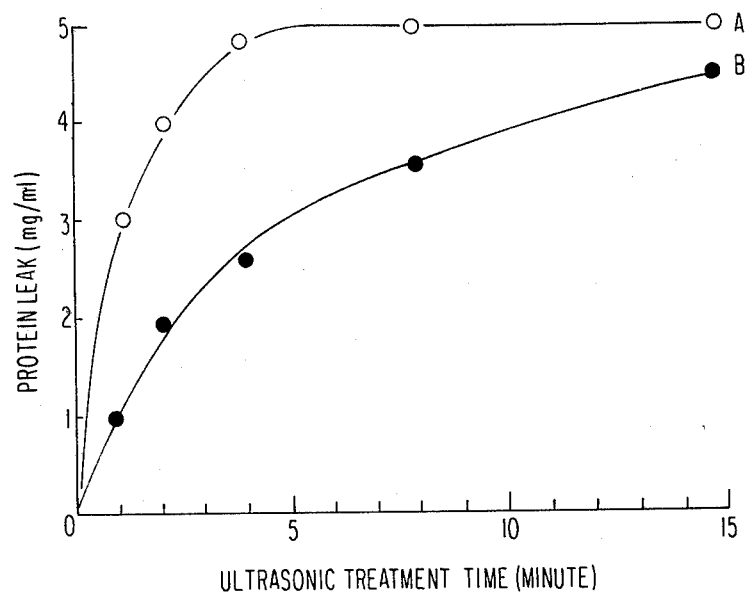
FIG. 2 is a graph showing the relation between ultrasonic treatment and protein leak, i.e., a graph showing a degree of a breaking tendency of the bacterial cell.

In Comparative Example 1, the procedure of Example 1 was repeated except that *Bacillus stearothermophilus* IAM 11001 was used. The results are represented in FIG. 2 which shows the relation between ultrasonic treatment and protein leak. In the figure, curve A represents Example 1 and curve B represents Comparative Example 1. As is clear from FIG. 2, the cells used in Example 1 could be broken and intracellular protein leaked by an ultrasonic treatment that lasted only about a fifth of the period required to break the cells used in Comparative Example 1. The protein leak was determined by the biuret method (see Gornall A. G., *Journal of Biological Chemistry*, Vol. 177, p. 751, 1949).

The cells broken by ultrasonic treatment contained 97.2 U of heat-resistant acetate kinase per gram of wet cell (1.2 U/mg of protein) and this figure was almost equal to the level (93.5 U/g wet cell) of heat-resistant acetate kinase in the cells obtained in Comparative Example 1.

EXAMPLE 2

Culture was performed in ten 500-ml conical flasks using a medium of the same composition as used in Example 1. The liquid cultures were combined, transferred to a 30-liter jar fermentor (MSJ-U Model of Marubishi Rika Sochi, using a flat blade turbine) that contained 20 liters also of a medium of the same composition as in Example 1, which had been sterilized with pressurized steam (121° C., 1 atm., 15 minutes), and subjected to fermentation at 60° C. and 400 rpm with air supplied at a rate of 20 liters/min. Cell growth was soon observed and a drop in pH occurred. The fermentation was continued for another 3 hours while 4 N NaOH was used to maintain the pH at 6.5. When the cell growth entered the last stage of the logarithmic growth phase, the culture was stopped and the medium was centrifuged at 8,000 G for 2 minutes to give 120 g of wet cells. The cells contained 105.3 U of heat-resistant acetate kinase per g of cell (1.3 U/mg of protein).

EXAMPLE 3

Batch culture was performed in a 30-liter jar fermentor in the same manner as in Example 1. When the cell growth entered the last stage of the logarithmic growth phase and the residual glucose level in the liquid culture was less than 0.01 wt.%, a chemostatic continuous fermentation was performed with the dilution ratio being held close to the maximum specific growth rate of the microorganism by supplying a fresh medium (of the same composition as used in Example 1) to the fermentor and withdrawing the fermentation liquor from the fermentor with a metering pump at a rate of 24 liters per hour. The other culture conditions were as follows: temperature, 60° C.; pH, 6.8-7.0 (controlled automatically with 4 N NaOH); air supply rate, 20 liters/min; and stirring speed; 600 rpm. During the fermentation, foaming occurred, so a defoaming agent (KM-70 of Shinetsu Chemical Industry Co., Ltd.) was added. Throughout the continuous fermentation, that lasted for about 4 hours, the cell concentration was maintained at the level achieved at the start of the fermentation (5.8 g of wet cell per liter or 0.75 g of dry cell per liter), and 550 g of wet cells were centrifuged from 96 liters of the fermentation liquor. The cells so obtained contained 130 U of heat-resistant acetate kinase per gram of wet cells (1.6 U per mg of protein). The cells harvested by continuous fermentation contained more heat-resistant acetate kinase per unit cell than those produced solely by batch processing.

While the invention has been described in detail and with reference to specific embodiments thereof, it will be apparent to one skilled in the art that various changes and modifications can be made therein without departing from the spirit and scope thereof.

What is claimed is:

1. A process for producing a heat-resistant acetate kinase that comprises culturing cells of Strain FERM-P No. 5141, a new strain of thermophilic *Bacillus stearothermophilus* having an appreciably elongated cell, and collecting a heat-resistant acetate kinase from the culture obtained.

2. A process according to claim 1, wherein the culturing is performed by a batch process until the cell growth has entered the last stage of the logarithmic growth phase.

3. A process according to claim 2, wherein continuous culture is performed with a dilution ratio held close to the maximum specific growth rate of a biologically pure culture of Strain FERM-P No. 5141.

4. A process as in claim 1 or 2, wherein the culturing is conducted in a liquid medium.

5. A process as in claim 3, wherein the culturing is conducted in a liquid medium.

6. A process as in claim 1 or 2, wherein the culturing is conducted aerobically for from about 2 to 6 hours at a temperature of from about 20° to 80° C.

7. A process as in claim 6, wherein the temperature is from 40° to 70° C.

8. A process as in claim 6, wherein the temperature is from 50° to 63° C.

9. A process as in claim 4, wherein the culturing is conducted aerobically for from about 2 to 6 hours at a temperature of from 20° to 80° C.

10. A process as in claim 9, wherein the temperature is from 40° to 70° C.

11. A process as in claim 9, wherein the temperature is from 50° to 63° C.

* * * * *